(12) United States Patent
Meudt et al.

(10) Patent No.: US 7,262,328 B1
(45) Date of Patent: Aug. 28, 2007

(54) METHOD FOR THE PRODUCTION OF ALDEHYDES AND KETONES BY OXIDIZING PRIMARY AND SECONDARY ALCOHOLS WITH ALKYLPHOSPHONIC ACID ANHYDRIDES

(75) Inventors: Andreas Meudt, Hofheim (DE); Stefan Scherer, Griesheim (DE); Claudius Boehm, Frankfurt (DE)

(73) Assignee: Archimica GmbH, Frankfurt am Main (DE)

( * ) Notice: Subject to any disclaimer, the term of this patent is extended or adjusted under 35 U.S.C. 154(b) by 0 days.

(21) Appl. No.: 10/592,439

(22) PCT Filed: Apr. 18, 2005

(86) PCT No.: PCT/EP2005/004093
§ 371 (c)(1),
(2), (4) Date: Sep. 12, 2006

(87) PCT Pub. No.: WO2005/002978
PCT Pub. Date: Nov. 3, 2005

(30) Foreign Application Priority Data
Apr. 22, 2004 (DE) .................. 10 2004 020 189

(51) Int. Cl.
*C07C 45/38* (2006.01)
*C07C 45/39* (2006.01)

(52) U.S. Cl. .................. 568/322; 361/403; 361/426; 361/485

(58) Field of Classification Search .................. None
See application file for complete search history.

(56) References Cited
OTHER PUBLICATIONS

Hsing-Jang Liu et al.; "Phenyl Dichlorophosphate as an Activating Agent in the Pfitzner-Moffatt Oxidation" Tetrahedron Letters. vol. 29, No. 26, 1988, pp. 3167-3170 XP002337769 Elsevier Science Publishers, Amsterdam, NL.

Wissmann H. et al.: "Oxidation of Alcohols by Activated Dimethy Sulfoxide and Related Reactions: an Update" Synthesis, Thieme, Stuttgart, Germany No. 10, Oct. 1990. pp. 857-870 XP000160078 ISSN: 0039-7881.

Anonymous: "T3P: The water scavenger. T3P (Propane Phosphonic Acid Anhydride) A versatile condensation reagent" Internet Article, 'Online! Jun. 1999, XP002337773.

*Primary Examiner*—Sikarl A. Witherspoon
(74) *Attorney, Agent, or Firm*—ProPat, L.L.C.

(57) ABSTRACT

The invention relates to a method for the production of a.) aldehydes of formula (II): $R^1$—CHO and b.) aldehydes of formula (III): $R^1$—C(O)—$R^2$ by reacting a.) primary alcohols ($R^1CH_2$—OH) or b.) secondary alcohols ($R^1$—CH(OH)—$R^2$) with cyclic phosphonic acid anhydrides in the presence of dialkyl-, diaryl- and/or alkyl-aryl sulphonic oxides at a temperature in the region of between −100 to +120° C., whereby $R^1$ and/or $R^2$ represent H, a substituted linear or branched $C_1$-$C_{12}$-alkyl radical, a substituted $C_3$-$C_{10}$ cycloalkyl-, alkenyl-, aryl- or heteroaryl radical. A cyclic phosphonic acid anhydride is used, preferably, as a 2,4,6-substituted 1,3,5,2,4,6-trioxatriphosphinane of formula (I), wherein R' independently represents allyl, aryl or open-chained or branched $C_1$-$C_{12}$-alkyl-radicals. Optionally, the reaction can be carried out in the presence of a tertiary amine base $NR^5_3$ (I)

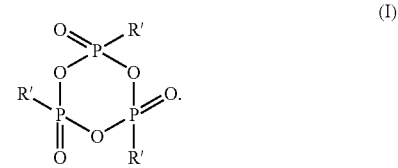

10 Claims, No Drawings

METHOD FOR THE PRODUCTION OF ALDEHYDES AND KETONES BY OXIDIZING PRIMARY AND SECONDARY ALCOHOLS WITH ALKYLPHOSPHONIC ACID ANHYDRIDES

CROSS-REFERENCE TO RELATED APPLICATIONS

This application is being filed under Rule 1.371 as a National Stage Application of pending International Application No. PCT/EP2005/004093, which claims priority to the following parent application: German Patent Application No. 10 2004 020 189.7 filed Apr. 22, 2004. Both International Application No. PCT/EP2005/004093 and German Patent Application No. 10 2004 020 189.7 are hereby incorporated by reference herein in their entirety.

FIELD OF THE INVENTION

Method for the production of aldehydes and ketones by oxidizing primary and secondary alcohols with alkylphosphonic acid anhydrides

BACKGROUND OF THE INVENTION

Aldehydes and ketones are important and extremely versatile intermediates in organic synthesis. Both compound classes exhibit a high reactivity of the C,O double bond, which enables numerous carbonyl reactions. The significance in modern organic synthesis is restricted only by limitations in the availability of these compound classes. Standard processes for preparing aldehydes and ketones are oxidations of corresponding alcohols, for which numerous methods such as catalytic vapor phase dehydrogenation or direct oxidation with molecular oxygen find use. It is also possible to use reagents such as hypohalic acids, heavy metal compounds such as silver carbonate, lead oxide, lead acetate, chromium oxides, ruthenates or else dimethyl sulfoxide, for example.

In modern organic synthesis, the significance of chemo-, regio- and stereoselective reagents is increasing explosively. When, for example, the intention is to convert a specific alcohol functionality to an aldehyde in a complex molecule with numerous functional groups, numerous methods from those mentioned, for example catalytic vapor phase dehydrogenation and direct oxidation with molecular oxygen, can no longer be used for selectivity reasons. The use of hypohalic acids is also restricted, since undesired side reactions such as overoxidation, halogenations or esterifications likewise occur, accompanied by low yields in some cases. The oxidation of primary alcohols to aldehydes or secondary alcohols to ketones with heavy metal compounds is always associated with the toxicity of the oxidizing agents in addition to the occurrence of by-products and the overoxidation.

There has to date been a lack of a highly selective solution to the problem of converting primary and secondary alcohols to the corresponding aldehydes and ketones, which can also be employed in complex multi-functional molecules. Although the known reagents can accomplish the desired transformations, other moieties are often likewise influenced. In many cases, the drastic conditions required epimerize even far-removed stereocenters. Moreover, the method to be developed should be heavy metal-free. In addition, the transformation should be employable under very mild conditions and the removal of the conversion products of the reagent used should be very simple.

It would therefore be very desirable to have a process which can convert primary and secondary alcohols by oxidation to the corresponding aldehydes and ketones but at the same time has very mild reaction conditions and a simplified workup, and is additionally usable in economically utilizable processes. The known reagents do not solve this problem, as will be demonstrated using some examples: although DMSO in combination with acetic anhydride can accomplish the reactions mentioned, this process only has restricted possible uses, since low yields are obtained in most cases. By-products are often formed in significant amounts, in particular via a Pummerer rearrangement. The oxidations of primary alcohols to aldehydes with DMSO in combination with trifluoroacetic anhydride can lead to explosions and must therefore be carried out at low temperatures at which, though, many complex molecules and natural substances are often no longer sufficiently soluble. The oxidation of primary alcohols with DMSO and thionyl chloride or oxalyl chloride must likewise be accomplished at low temperatures. However, these reagents can no longer be used when the molecules to be oxidized contain functional groups which can react with thionyl chloride or oxalyl chloride. It is likewise possible to carry out the desired transformation to aldehydes with DCC. However, the dicyclohexylurea formed as a conversion product can often barely be removed from the product or only by increased purification complexity. The use of water-soluble DCC derivatives is usually characterized by their very high cost, the instability of the intermediates in the oxidation and reduced effectiveness of the oxidizing agent.

SUMMARY OF ADVANTAGEOUS EMBODIMENTS OF THE INVENTION

It has been found that, surprisingly, the combination of cyclic 2,4,6-substituted 1,3,5,2,4,6-trioxa-triphosphinanes and sulfoxides solves all of these problems. This combination is a highly selective oxidation method for the conversion of primary alcohols to the corresponding aldehydes and of secondary alcohols to the corresponding ketones, the desired freedom from epimerization and maximum regio- and stereoselectivity being observed at the same time with simultaneously virtually quantitative yields.

DETAILED DESCRIPTION OF ADVANTAGEOUS EMBODIMENTS OF THE INVENTION

The present invention thus relates to a highly selective process for preparing a.) aldehydes of the formula (II) and b.) ketones of the formula (III)

by reacting a.) primary alcohols ($R^1CH_2$—OH) or b.) secondary alcohols ($R^1$—CH(OH)—$R^2$)

with cyclic alkylphosphonic anhydrides in the presence of dialkyl sulfoxides, diaryl sulfoxides or alkyl aryl sulfoxides and optionally an amine base $NR_3$ at a temperature in the range from −100 to +120° C., where $R^1$ and/or $R^2$ are each an optionally substituted linear or branched $C_1$-$C_{12}$-alkyl radical, substituted $C_3$-$C_{10}$-cycloalkyl, -alkenyl, -aryl or -heteroaryl radicals.

In a preferred inventive embodiment, the cyclic phosphonic anhydride is a 2,4,6-substituted 1,3,5,2,4,6-trioxatriphosphinane of the formula (I)

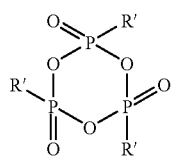

where R' is independently allyl, aryl or open-chain or branched $C_1$- to $C_{12}$-alkyl radicals, in particular $C_1$-$C_8$-alkyl radicals.

Particular preference is given to phosphonic anhydrides of the formula (I) in which R' is a methyl, ethyl, n-propyl, isopropyl, n-butyl, 2-butyl, isobutyl, pentyl, hexyl, in particular an ethyl, propyl and/or butyl radical.

The oxidation to aldehydes (II) and ketones (III) can be carried out generally at temperatures in the range from −100 to +120° C., preference being given to temperatures in the range from −30 to +30° C., lower temperatures generally being correlated with higher selectivities. The reaction time is dependent upon the temperature employed and is generally from 1 to 12 hours, in particular from 3 to 6 hours.

The sulfoxides used are generally dialkyl sulfoxides, diaryl sulfoxides or alkylaryl sulfoxides of the formula (IV)

where $R^3$ and $R^4$ are each independently allyl, aryl or open-chain, cyclic or branched $C_1$- to $C_{12}$-alkyl radicals, aryloxy, allyloxy or alkoxy having open-chain, cyclic or branched $C_1$- to $C_{12}$-alkyl radicals, or a combination of the substituents mentioned.

Particular preference is given to sulfoxides of the formula (IV) in which $R^3$ or $R^4$ is a methyl, ethyl, n-propyl, isopropyl, n-butyl, 2-butyl, isobutyl, pentyl, hexyl, phenyl, in particular a methyl and/or phenyl or a combination of the substituents mentioned.

The addition of amines is generally not required, but may prove to be advantageous in the individual case. The amines used are generally amines of the formula (V)

where $R^5$ is H, allyl, aryl or open-chain, cyclic or branched $C_1$- to $C_{12}$-alkyl radicals, aryloxy, allyloxy or alkoxy having open-chain, cyclic or branched $C_1$- to $C_{12}$-alkyl radicals, or a combination of the substituents mentioned.

Particular preference is given to amines of the formula (V) in which $R^5$ is an H, methyl, ethyl, n-propyl, isopropyl, n-butyl, 2-butyl, isobutyl, pentyl, hexyl, phenyl, in particular an H, ethyl, n-propyl, isopropyl, n-butyl, 2-butyl, isobutyl or phenyl, or a combination of the substituents mentioned.

The cyclic phosphonic anhydride can be added to the reaction medium either as a melt or as a liquid mixture dissolved in a solvent.

Suitable solvents are those which do not give rise to any side reactions with the phosphonic anhydride; these are all aprotic organic solvents, for example ligroin, butane, pentane, hexane, heptane, octane, cyclobutane, cyclopentane, cyclohexane, cycloheptane, cyclooctane, dichloromethane, chloroform, carbon tetrachloride, 1,2-dichloroethane, 1,1,2,2-tetrachloroethane, methyl acetate, ethyl acetate, propyl acetate, butyl acetate, dimethylformamide, diethylformamide, dimethylacetamide, diethylacetamide, diethyl ether, diisopropyl ether, tert-butyl methyl ether, THF, dioxane, acetonitrile or mixtures thereof; particular preference is given to dichloromethane, chloroform, ethyl acetate, propyl acetate, butyl acetate, dimethylformamide, diethylformamide, dimethylacetamide, diethylacetamide, diisopropyl ether, tert-butyl methyl ether, THF, dioxane, acetonitrile or mixtures thereof; very particular preference is given to dichloromethane, chloroform, ethyl acetate, butyl acetate, dimethylacetamide, tert-butyl methyl ether, THF, dioxane, acetonitrile or mixtures thereof; especially preferred are THF, ethyl acetate or butyl acetate.

The phosphonic anhydride is added generally in at least one third of the stoichiometric amount in relation to the starting compound, but may also be added in a superstoichiometric amount, for example in a ratio of 1 alcohol 1.2 T3P® (cyclic propanephosphonic anhydride).

The reactions are preferably carried out in such a way that the corresponding alcohol is initially charged in a solvent, then admixed with a dialkyl sulfoxide, diaryl sulfoxide or alkyl aryl sulfoxide, for example DMSO (dimethyl sulfoxide), and heated to the reaction temperature, preferably before the phosphonic anhydride is added. Subsequently, the alcohol is converted to the desired aldehyde or the desired ketone by metering in the phosphonic anhydride as a melt or solution in one of the aforementioned solvents.

The reaction product is preferably isolated by hydrolysis and simple phase separation, since the conversion products of the phosphonic anhydrides are generally very water-soluble. Depending on the nature of the product to be isolated, post-extractions may also be required. The phosphonic anhydride conversion product formed often does not disrupt subsequent reactions, so that even the direct use of the resulting reaction solutions often brings very good results.

All procedures mentioned are notable for very good yields (typically 90-100%, in particular >95%) in the simultaneous absence of side reactions and epimerizations. The selectivities of the inventive reaction are in the range of 99-100%, in particular >99.5%.

The process according to the invention will be illustrated in detail by the examples which follow without restricting the invention thereto:

EXAMPLE 1

Oxidation of Benzyl Alcohol to Benzaldehyde 1 mol of benzyl alcohol is initially charged in 50 ml of ethyl acetate and 50 ml of DMSO and cooled to 0° C. 1.2 mol of T3P solution in ethyl acetate (50% w/w) are metered in while maintaining the reaction temperature, then the mixture is stirred at this temperature for a further three hours. At this time, the reaction GC indicated a conversion of 100%. After warming to room temperature, 180 ml of water were added and the phases were separated. After the solvent had been condensed off, the benzaldehyde remained in a yield of 97%, HPLC purity 98% (a/a).

EXAMPLE 2

Oxidation of 3-buten-1-ol to 3-butenal 0.1 mol of 3-buten-1-ol is initially charged in 50 ml of ethyl acetate and 50 ml of DMSO and cooled to 0° C. 0.12 mol of T3P solution in ethyl acetate (50% w/w) is metered in while maintaining the reaction temperature, then the mixture is stirred at this temperature for a further two hours. At this time, the reaction GC indicated a conversion of >99%. After warming to room temperature, 25 ml of water were added and the phases were separated. The organic phase was distilled. The isolated yield of this reaction was 96%.

EXAMPLE 3

Oxidation of 2-butanol to 2-butanone 1 mol of 2-butanol is initially charged in 50 ml of butyl acetate and 50 ml of DMSO and cooled to 0° C. 1.2 mol of T3P solution in butyl acetate (50% w/w) are metered in while maintaining the reaction temperature, then the mixture is stirred at this temperature for a further three hours. At this time, the reaction GC indicated a conversion of 100%. After warming to room temperature, 180 ml of water were added and the phases were separated. The organic phase was distilled. The isolated yield was 97%.

EXAMPLE 4

Oxidation of N-(tert-butyloxycarbonyl)-threonine methyl ester to Boc-(S)-α-acetylglycine methyl ester 1 mol of N-(tert-butyloxycarbonyl)threonine methyl ester is initially charged in 50 ml of ethyl acetate and 50 ml of DMSO and cooled to 0° C. 1.2 mol of T3P solution in ethyl acetate (50% w/w) are metered in while maintaining the reaction temperature, then the mixture is stirred at this temperature for a further three hours. At this time, the reaction GC indicated a conversion of 100%. After warming to room temperature, 180 ml of water were added and the phases were separated. The aqueous phase was extracted twice with dichloromethane. After the combined organic phases had been dried over MgSO$_4$ and the solvents had been distilled off as gently as possible, the product remained in a yield of 97%.

What is claimed is:

1. A process for preparing a.) aldehydes of the formula (II) and b.) ketones of the formula (III)

said process comprising reacting a reaction solution comprising a starting compound selected from
a.) primary alcohols (R$^1$CH$_2$—OH) or
b.) secondary alcohols (R$^1$—CH(OH)—R$^2$)
with cyclic phosphonic anhydrides in the presence of dialkyl sulfoxides, diaryl sulfoxides and/or alkyl aryl sulfoxides at a temperature in the range from −100 to +120° C.,
where R$^1$ and/or R$^2$ are each a substituted linear or branched C$_1$-C$_{12}$-alkyl radical, a substituted C$_3$-C$_{10}$-cycloalkyl, -alkenyl, -aryl or -heteroaryl radical.

2. The process as claimed in claim 1, wherein the cyclic phosphonic anhydride is a 2,4,6-substituted 1,3,5,2,4,6-trioxatriphosphinane of the formula (I)

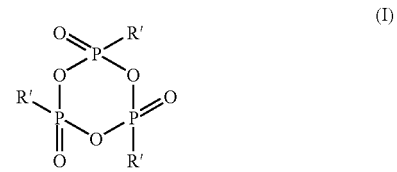

where R' is independently allyl, aryl or open-chain or branched C$_1$- to C$_{12}$-alkyl radicals.

3. The process as claimed in claim 2, wherein R' is a methyl, ethyl, n-propyl, isopropyl, n-butyl, 2-butyl, isobutyl, pentyl, and/or hexyl, radical.

4. The process as claimed in claim 1 wherein the cyclic phosphonic anhydride is added to the reaction solution either as a melt or dissolved in a solvent.

5. The process as claimed in claim 4, wherein the cyclic phosphonic anhydride is added in an aprotic solvent.

6. The process as claimed in claim 1 wherein the reaction solution is heated to the reaction temperature before the phosphonic anhydride is added.

7. The process as claimed in claim 1 wherein a sulfoxide of the formula (IV) is used

where R$^3$ and R$^4$ are each independently allyl, aryl or open-chain, cyclic or branched C$_1$- to C$_{12}$-alkyl radicals, aryloxy, allyloxy or alkoxy having open-chain, cyclic or branched C$_1$- to C$_{12}$-alkyl radicals, or a combination of the substituents mentioned.

8. The process as claimed in claim 1 characterized in that wherein the reaction is carried out in the presence of an amine base of the formula (V)

where R$^5$ is H, allyl, aryl or open-chain, cyclic or branched C$_1$- to C$_{12}$-alkyl radicals, aryloxy, allyloxy or alkoxy having open-chain, cyclic or branched C$_1$- to C$_{12}$-alkyl radicals, or a combination of the substituents mentioned.

9. The process as claimed in claim 1 wherein the phosphonic anhydride is used in from one third of the stoichiometric amount to a superstoichiometric amount in relation to the starting compound.

10. The process as claimed in claim 3, wherein R' is an ethyl, propyl and/or butyl radical.

* * * * *

UNITED STATES PATENT AND TRADEMARK OFFICE
CERTIFICATE OF CORRECTION

PATENT NO. : 7,262,328 B1
APPLICATION NO. : 10/592439
DATED : August 28, 2007
INVENTOR(S) : Meudt et al.

Page 1 of 1

It is certified that error appears in the above-identified patent and that said Letters Patent is hereby corrected as shown below:

Column 5
Line 54, delete "$R^1$-C(O)-R" and insert -- $R^1$-C(O)-$R^2$ --

Signed and Sealed this

Sixth Day of November, 2007

JON W. DUDAS
*Director of the United States Patent and Trademark Office*